United States Patent [19]

Brown

[11] Patent Number: 5,037,425
[45] Date of Patent: Aug. 6, 1991

[54] DEVICE AND METHOD FOR CEMENTING A HIP PROSTHESIS IN A FEMORAL CANAL

[76] Inventor: Byron L. Brown, 2315 Hendricks, Fort Smith, Ak. 72903

[21] Appl. No.: 734,559

[22] Filed: May 16, 1985

[51] Int. Cl.$^5$ ............................ A61F 2/36; A61F 2/32
[52] U.S. Cl. ......................................... 606/92; 606/94
[58] Field of Search ...................... 623/23, 22, 20, 18, 623/16; 128/92 H, 92 EB, 92 A; 408/115 R, 97, 241 B, 241 G

[56] References Cited

U.S. PATENT DOCUMENTS 3,877,424  4/1975  Murray .............................. 128/92 A
3,941,123  3/1976  Volkov et al. ............... 128/92 A X Primary Examiner—Alan Cannon

[57] ABSTRACT

An improved U-shaped base guide for rigid attachment to the proximal end of a femur with at least one pin through the femoral cortex to enable cement to be applied to the femoral canal under pressure and having at least a first orifice in one side of the U-shaped guide and a second orifice in another side of the U-shaped guide in axial alignment with the first orifice. The second orifice is larger in cross-section than the attaching pin and an insert easily penetrable by the attaching pin is removably placed in the second orifice whereby the attaching pin in passing through the first orifice, the femoral cortex and the easily penetrable insert may deviate from axial alignment between the first and second orifices without striking the base guide.

12 Claims, 1 Drawing Sheet

5,037,425

DEVICE AND METHOD FOR CEMENTING A HIP PROSTHESIS IN A FEMORAL CANAL

BACKGROUND OF THE INVENTION

The present invention relates to a method and apparatus for mounting a femoral stem hip prosthesis in a femoral canal with the use of a cement. In U.S. Pat. No. 4,357,716, issued Nov. 9, 1982, it is pointed out that there are a great many problems involved in mounting the femoral stem hip prosthesis in the femoral canal with the use of cement and there is disclosed therein a device which holds the prosthesis in a fixed position relative to the femur while cement is applied to the femoral canal under pressure and allowed to set.

This device requires the use of a base guide which is rigidly attached to the femur and which not only enables the surgeon to determine the proper angle at which to resect the head and neck of the femur but also provides the base for attachment of other components which enable cement to be applied to the femoral canal under pressure. The base guide is attached to the femur in the location of the lesser trochanter with pins extending through portions of the cortex of the femur. These pins may be Kirschner wires or any other fixation device such as Steinmann pins or small drill bits and the like. The base guide is generally U-shaped and has orifices in each side thereof that are opposed and axially aligned. The pins pass through the orifice in one side, the femoral cortex and the opposing orifice in the other side of the guide.

The orifices are made only slightly larger than the Steinmann pins and while this method and apparatus performs the function for which it was intended, it has been found that if there is any slight misalignment of the pin as it passes through the femoral cortex, it may not precisely line up with the orifice on the opposite side of the U-shaped guide. Thus, the pin may strike the guide itself instead of the orifice thereby requiring the pin to be reset. Not only, then, is a problem created in getting the pin to pass directly in alignment from one orifice to the other but also increased time for the surgery is required.

The present invention overcomes this disadvantage by providing a first orifice in the guide for inserting a pin and a second opposing orifice in the guide much larger in cross section than the pin and inserting in the second receiving orifice an easily penetrable material such as a cylindrical plastic plug whereby the pin in passing through the first inserting orifice and the femoral cortex, may deviate from axial alignment and still strike the plastic plug in the receiving orifice and pass therethrough. Thus, the metal frame of the base guide is not touched and yet the pin may deviate somewhat from the axial alignment and still penetrate the plastic plug. The plastic plug is threaded and so is the second receiving orifice in which it is inserted so that after the base guide has been used in one operation, the plastic plug can be threadably removed and a new one threadably inserted so that the guide can be used again in the next operation.

In addition, instead of using Kirschner pins or Steinmann pins, an elongated drill bit having approximately the same outside diameter as the Kirschner or Steinmann pins are used. Thus, by using the small drill not only does the drill bit pass easily through the femoral cortex with a minor amount of deviation but it also easily penetrates the plastic plug in the second receiving orifice thus enabling the base guide to be securely attached to the femur in a rigid relationship. Obviously, other opposed pairs of axially aligned orifices could be placed in said U-shaped guide as disclosed in U.S. Pat. No. 4,357,716 wherein the receiving of the orifices is larger than the attaching pin and has a cylindrical plastic plug removably threaded therein to allow a drill bit, serving as an attaching pin, to pass from the first pin insertion orifice to the second pin receiving orifice with deviation from the axial alignment without striking the metal guide.

Thus, it is an object of the present invention to provide an improved U-shaped base guide for rigid attachment with at least one pin through the femoral cortex to the proximal end of a femur as a guide for removing the neck of said femur.

It is also an object of the present invention to provide at least a first pin insertion orifice in one side of the U-shaped guide, a second pin receiving orifice in the opposite side of the U-shaped guide in axial alignment with the first orifice and a plastic plug threadedly inserted in the second orifice and being easily penetrable by the pin so that the pin may deviate from axial alignment between the first and second orifices without striking the base guide.

It is also an object of the present invention to use a drill bit in place of a Kirschner pin or a Steinmann pin so that penetration of the femoral cortex and of the plastic plug insert in the second orifice is more easily accomplished.

SUMMARY

Thus, the present invention relates to an improved U-shaped base guide for rigid attachment to the proximal end of a femur with at least one pin through the femoral cortex and being used as a guide for removing the neck of said femur comprising at least a first orifice in one side of said U-shaped guide, at least a second orifice in the opposite side of said U-shaped guide in axial alignment with said first orifice, said second orifice being larger in cross section than said attachment pin, and means inserted in said second orifice easily penetrable by said pin whereby said pin in passing through said first orifice, said femoral cortex and said easily penetrable means in said second orifice may deviate from axial alignment between said first and second orifices without striking the base guide.

It is also an object of the present invention to provide an improved method of cementing a hip prosthesis in a femoral canal using a generally U-shaped base guide which is rigidly attached to the proximal end of a femur by pins passing through opposed orifices on opposite sides of the guide thereby forming a guide for removing the neck of said femur, said improved method of forming said base guide comprising the steps of forming a first orifice in one side of the U-shaped base guide for insertion of an attaching pin therein, forming an opposing axially aligned second orifice on the opposite side of said U-shaped guide for receiving said pin after it passes through said femoral cortex, said pin receiving orifice having a diameter greater than the diameter of said attaching pin, and removably inserting a relatively rigid material easily penetrable by said pin in said second pin receiving orifice whereby an area much larger than the cross sectional area of said pin will be formed for receiving and passing said pin therethrough when it is inserted from said first orifice to said easily penetrable means in said second orifice thereby allowing deviation of said pin from a straight line from said first to said second orifice without striking the body of said U-shaped guide.

BRIEF DESCRIPTION OF THE DRAWINGS

These and other objects and advantages of the present invention will be disclosed in the course of the following specification, reference being had to the accompanying drawings in which.

DETAILED DESCRIPTION OF THE DRAWINGS

Figures 1, 2, 3, 4:
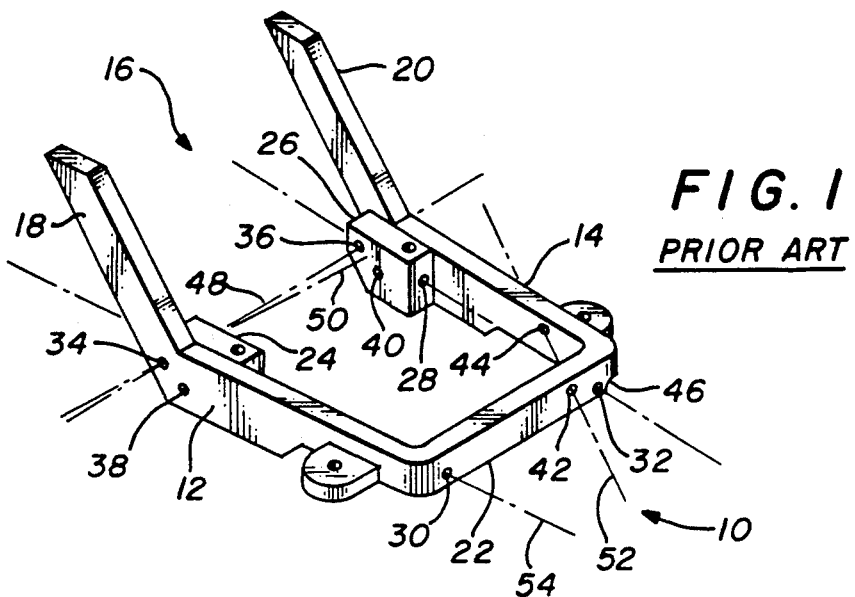
FIG. 1 is an isometric view of the base guide disclosed in U.S. Pat. No. 4,357,716 illustrating the opposing pairs of orifices therein through which pins may be inserted to attach the base guide rigidly to the femur.
FIG. 2 is an isometric view of the base guide of the present invention illustrating the manner in which plastic cylindrical plugs may be inserted in an orifice in one side of the base guide to receive the pin while allowing the pin to deviate from the axial alignment of the first and second orifices.
FIG. 3 is a partial isometric view of a base guide illustrating the manner in which the pin may deviate horizontally from the axial alignment of the two opposed orifices and still penetrate the plastic cylindrical plug which is inserted in the orifice in one side of the base guide.
FIG. 4 is an illustration of how the pin can deviate in the vertical direction from the axial alignment of the two opposed orifices and still penetrate the plastic plug which is inserted in one of the orifices.

As shown in FIG. 1, base guide 10 is, roughly speaking, U-shaped or horseshoe-shaped. The sides, 12 and 14, at the open end 16 have wings 18 and 20 which are angulated upwardly by approximately 41 degrees from the horizontal sides 12 and 14 and closed end 22. The exterior surface of closed end 22, wings 18 and 20 and sides 12 and 14 may be made of material sufficiently strong to maintain its form and resist cutting and bending while at the same time being suitable for medical use. Examples are plastics and metals, particularly surgical stainless steel. Sides 12 and 14 and closed portion 22 and wings 18 and 20 may be integrally formed. From a point midway between the sides of base guide 10 at the open end thereof to the midpoint of the inneraspect or innerside of the closed end 22, the distance is approximately 4.3 centimeters, for example, for a small femur. Also, for the small femur the distance across open end 16 is approximately 3.2 centimeters. It will be evident, of course, that various sizes and right and left base guides will be sufficient to provide for different size femurs, i.e. adult, child, and the like.

On the inner aspect of base guide 10 at the junction of wings 18 and 20 with horizontal sides 12 and 14, respectively, are supports 24 and 26 which may be made of metal or plastic. The upper surface of supports 24 and 26 are on a level with the upper or superior surface of the horizontal sides 12 and 14. The inferior or bottom surfaces of supports 24 and 26 are in the same plane as the bottom or inferior surface of the corresponding abutting wings 18 and 20 and corresponding abutting horizontal sides 12 and 14. The superior or upper surfaces of supports 24 and 26 are approximately 1.2 centimeters in length and 0.5 centimeters in width for a small femur, for example, and may be an integral part of base guide 10 or a small localized enlargement of base guide 10.

An orifice 28 runs longitudinally through each support 24 and 26 for the insertion of a 0.45 Kirschner wire from the back or posterior aspect of the support. One of these K wires may or may not be drilled into the lesser trochanteric region of the femur and pierces the closed end 22 of the base guide 10 through orifice 30. The K wire extending through orifice 28 and the lesser trochanter of the femur may pass through the femur and pierce orifice 32 located in the closed end 22 of the base guide 10. In some instances, orifices 28 and 32 may not be needed. Transverse orifices 34 and 36 pass through supports 24 and 26 and wings 18 and 20. These orifices are in axial alignment with each other and are for the insertion of a Kirschner wire usually size 0.62 which corresponds to approximately 1/16th inch in diameter and which passes through the base guide 10 in the cortices of the femur. It is preferred to have a second set of orifices, 38 and 40, which also pass through supports 24 and 26 and wings 18 and 20. This can be used in the event the base guide has to be realigned for proper placement of the prosthesis to permit placement of wires sufficiently distant from the openings in the bone made by the initial insertion of the wires to ensure rigid placement of the base guide 10. An oblique orifice 44 passes through the side 14 posterior to the lesser trochanteric area and is directed to an oblique orifice 42 located in the closed end 22 lateral to notch 46 for the lesser trochanter. These two orifices 42 and 44 are for 0.62 Kirschner wires or other fixation devices such as Steinmann pins, and the like, which also pass through the cortices of the femur posterior and lateral to the lesser trochanteric area, respectively, and these orifices are in direct alignment with each other.

It will be obvious that if the pin 48, after it passes through orifice 34 and support 24, is deflected for any reason such as striking the bone, it may deviate from the axial alignment and take a path as shown, for instance, at 50. In such case, the pin strikes the support 26 instead of the orifice 36. This may cause some difficulty and require that the pin 48 be withdrawn and reinserted in an effort to exactly strike orifice 36. Of course, this same problem occurs in aligning any of the other pins such as pin 52 or pin 54. If a drill bit is used as the pin and is drilled through the sides 12 and 14, the base guide 10, whether metal or plastic, would be quickly ruined and have to be replaced after a few holes were drilled in it.

FIG. 2 illustrates the base guide utilizing the present invention which allows the drill bit to be inserted from one side of the base guide 10 through the femoral cortex and through the other side of the base guide 10 without striking the metal base guide itself. A large orifice 55 is formed in side 14 of the base guide and a plastic plug 56 or other material that is easily penetrable by said pin 48 is threadably inserted therein. When pin 48 passes through an orifice 68 in side 12 of the base guide and through the femoral cortex, if any misalignment occurs, the pin can still pass through the easily penetrable material, such as plastic plug 56, and through side 14 of the base guide without striking side 14. This is shown more clearly in FIG. 3 wherein pin 48 passes through orifice 68 of side 12 of the base guide 10 and if it is in direct axial alignment with the orifice 55 in side 14 it penetrates the plastic plug 56 at 58. If, however, it deviates in the horizontal direction to the right it passes through the easily penetrable material or plastic plug 56 at 60. In like manner, if it deviates to the left it passes through the plastic plug 56 at 62. Thus, it can be seen that a rather large deviation of the travel path of pin 48 can be accommodated simply by placing the plastic plug 56 in side 14 by threading it in orifice 55.

It may be necessary to cause pin 48 to be passed through the base guide 10 in the opposite direction from side 14 to side 12. If that is the case, the base guide 10 can be made a universal base guide by enlarging orifice 64 in side 12 and making it the same diameter as orifice 55 in side 14. A plug 66 can be threadably inserted in orifice 64 with a third orifice 68 centrally located in the plug 66 parallel to orifice 64 for receiving the pin 48. This allows plug 66 and plastic plug 56 to be placed in either side 12 or 14 of the base guide thus allowing the pin 48 to be inserted from either side. If plug 66 is made of metal, the insertion and rotation of the pin 48 will not wear it out as quickly as if it were plastic. Thus, the use of a metal plug 56 will provide a longer lasting support for the pin 48.

Of course, pins 52 and 54 as shown in FIG. 1 can also be accommodated with the plastic and metal plugs 56 and 66 as illustrated in FIG. 2 by pin 52. In like manner, as shown in FIG. 2 pin 74 is inserted through metal plug 70 and plastic plug 72 from side 12 of the base guide through side 14. Again, it will be understood that metal plug 70 and plastic plug 72 could reverse positions so that the pin 74 could be inserted from side 14 instead of side 12.

In order that the pin may more easily pass through the plastic plug, a drill bit could be used as pin 74. Thus, by placing the drill bit in a chuck and passing it through metal plug 70, the bit will easily penetrate the femoral cortex and strike plastic plug 72.

FIG. 4 illustrates the vertical deviation of pin or drill bit 48 as it passes through the orifice 68 of metal plug 66 to the plastic plug 56. If it happens to be axially aligned it would emerge at 76 whereas if it deviates vertically it would penetrate at 78 whereas if it deviated downwardly in the vertical direction it would exit at 80.

Thus, there has been disclosed a novel means for allowing a base guide to be utilized for rigid attachment to a femur as a guide for removing the neck of the femur with at least one pin passing through the femoral cortex to the proximal end of a femur. The present invention thus allows the use of a pin to go from one side of the base guide to the other while passing through the femoral cortex to cause the base guide to be rigidly attached thereto. By the use of an easily penetrable material such as a plastic plug, the invention allows the use of a pin such as a drill bit to deviate from the axially aligned path and still pass through the plastic plug without striking the base guide itself. By making a metal plug for the support for the drill bit on one side and the plastic plug for the other side and making the two plugs of the same diameter, they can be interchanged thus allowing the drill bit or pin to be inserted from either side of the base guide thus making it universal. Further, the plastic plug can be discarded after it is used allowing a new plastic plug to be inserted and the process repeated with another patient using the same base guide.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. An improved U-shaped base guide body for rigid attachment with at least one pin through the femoral cortex to the proximal end of a femur to enable cement to be applied to the femoral canal under pressure comprising:
   a. at least a first orifice in one side of said U-shaped guide body,
   b. at least a second orifice in another side of said U-shaped guide body in axial alignment with said first orifice, said second orifice being larger in cross-section than said attaching pin, and
   c. means inserted in said second orifice easily penetrable by said pin whereby said pin, in passing through said first orifice, said femoral cortex, and said easily penetrable means in said second orifice, may deviate from axial alignment between said first and second orifices without striking the base guide body.

2. A guide as in claim 1 wherein said easily penetrable means inserted in said second orifice is a cylindrical plastic plug.

3. A guide as in claim 2 further including:
   a. threads in said second orifice, and
   b. matching threads on said cylindrical plastic plug whereby said plug may be removably threaded into said second orifice thereby enabling a used plug to be removed and replaced with a new plug.

4. A guide as in claim 3 further including an elongated drill bit as said pin whereby said drill bit may easily penetrate said femoral cortex and said plastic plug.

5. A guide as in claim 4 further including:
   a. said first orifice having the same diameter as said second orifice and having threads therein;
   b. an elongated cylindrical metal plug for removable threaded insertion in said first or second orifice, and
   c. a third orifice centrally located in said metal plug parallel to said elongation for receiving said drill bit whereby said plastic plug and said metal plug may be removably threaded into either said first or second orifice thereby enabling said drill to be inserted through said guide in either direction.

6. A guide as in claim 5 further comprising at least one other axially aligned opposed pair of orifices in said U-shaped guide for threadably receiving said cylindrical plastic plug and said cylindrical metal plug to allow a drill bit to pass from a first one of said other opposed orifices to the second to accommodate deviation of said drill bit from said axial alignment without striking said guide.

7. An improved U-shaped metal base guide for rigid attachment to the proximal end of a femur to enable cement to be applied to the femoral canal under pressure and comprising:
   a. first and second aligned opposed orifices in said U-shaped guide respectively for inserting and receiving a pin passing through the cortex of said femur, said second orifice having a greater diameter than said pin,
   b. screw threads on the inside of said second orifice, and
   c. a relatively rigid plug of material easily penetrable by said pin and removably threaded into said second orifice whereby an area much larger than the cross-sectional area of said pin is formed for receiving and passing said pin therethrough when it is inserted from said first orifice and passed through said femoral cortex to said second orifice thereby allowing deviation of said pin from a straight line from said first orifice to said second orifice without striking the metal of said U-shaped guide.

8. In a method of cementing a hip prosthesis in a femoral canal using a generally U-shaped base guide which is rigidly attached to the proximal end of a femur by pins passing through opposed orifices on opposite sides of said guide thereby forming a guide for enabling cement to be applied to the femoral canal under pressure, an improved method of forming said base guide comprising the steps of:
   a. forming a first orifice in one side of said U-shaped base guide for insertion of an attaching pin therein,
   b. forming an opposing axially aligned second orifice in another side of said U-shaped guide for receiving said pin after it passes through said femoral cortex, said second orifice having a diameter greater than the diameter of said attaching pin, and
   c. removably inserting a relatively rigid material easily penetrable by said pin in said second orifice whereby an area much larger than the cross-sectional area of said pin will be formed for receiving and passing said pin therethrough when it is inserted from said first orifice to said easily penetrable means in said second orifice thereby allowing deviation of said pin from a straight line from said first to said second orifice without striking said U-shaped guide.

9. A method as in claim 8 further including the step of forming said easily penetrable material in the shape of a cylindrical plastic plug.

10. A method as in claim 9 further including the steps of:
   a. forming threads in said second orifice, and
   b. threading said plastic plug therein whereby said plug may be removed after use and replaced with a new plug for the next use.

11. A method as in claim 10 further including the step of using an elongated drill bit as said pin for passing through said plastic plug.

12. A method as in claim 11 further including the steps of:
   a. enlarging and threading said first orifice,
   b. threading an elongated metal plug in said first orifice, and
   c. forming a centrally located third orifice in said metal plug parallel to said elongation for receiving said drill bit whereby either said plastic plug or said cylindrical metal plug may be threadably inserted in either said first or second orifices thereby enabling said drill bit to be inserted from either side of said guide.

* * * * *